(12) United States Patent
Kurek et al.

(10) Patent No.: US 8,641,667 B2
(45) Date of Patent: Feb. 4, 2014

(54) PERFUSION DEVICE AND METHOD

(75) Inventors: Ed Kurek, North Wales, PA (US); Sean H. Kerr, Oreland, PA (US)

(73) Assignee: DePuy Synthes Products, LLC, Raynham, MA (US)

( * ) Notice: Subject to any disclaimer, the term of this patent is extended or adjusted under 35 U.S.C. 154(b) by 149 days.

(21) Appl. No.: 12/089,679

(22) PCT Filed: Oct. 19, 2006

(86) PCT No.: PCT/US2006/041202
§ 371 (c)(1),
(2), (4) Date: Apr. 9, 2008

(87) PCT Pub. No.: WO2007/048016
PCT Pub. Date: Apr. 26, 2007

(65) Prior Publication Data
US 2008/0214998 A1  Sep. 4, 2008

Related U.S. Application Data

(60) Provisional application No. 60/729,167, filed on Oct. 20, 2005.

(51) Int. Cl.
*A61M 1/00* (2006.01)
(52) U.S. Cl.
USPC .......................................... 604/125; 604/122
(58) Field of Classification Search
USPC .......... 604/131, 93.01, 181, 183, 82–90, 186; 433/90
See application file for complete search history.

(56) References Cited

U.S. PATENT DOCUMENTS 2,337,149 A    12/1943  Bullock
(Continued)

FOREIGN PATENT DOCUMENTS

| CA | 24198500 | 2/2002 |
| CN | 1251046 | 4/2000 |

(Continued)

OTHER PUBLICATIONS

"International Search Report for Application No. PCT/US2006/41202, date mailed Sep. 26, 2007", 5 pgs.

(Continued)

*Primary Examiner* — Manuel Mendez
*Assistant Examiner* — Jenna Zhang
(74) *Attorney, Agent, or Firm* — Woodcock Washburn LLP

(57) ABSTRACT

A perfusion device and method is provided in various examples. In an example, the device includes a container having a first internal chamber configured to hold the material; a port for introducing the liquid into the chamber; a vent for releasing gas and liquid from the chamber; and a flow control device for sealing the vent to allow a vacuum to be drawn on the first chamber. In an example, the container includes a syringe that defines the internal material chamber and includes an end cap and a plunger. The vent may be formed by a venting passageway in the plunger and/or the cap. In various examples, the vacuum may be created by a medical syringe coupled to the container. In some examples, the medical syringe may also be used to deliver the liquid into the container.

9 Claims, 12 Drawing Sheets

(56) References Cited

U.S. PATENT DOCUMENTS

| | | | |
|---|---|---|---|
| 4,226,236 A * | 10/1980 | Genese | 604/89 |
| 4,529,511 A | 7/1985 | Breeden et al. | |
| 4,690,154 A * | 9/1987 | Woodford et al. | 600/578 |
| 4,758,096 A | 7/1988 | Gunnarsson | |
| 4,808,184 A | 2/1989 | Tepic | |
| 4,842,581 A | 6/1989 | Davis | |
| 4,935,010 A * | 6/1990 | Cox et al. | 604/122 |
| 5,051,482 A | 9/1991 | Tepic | |
| 5,139,031 A | 8/1992 | Guirguis | |
| 5,164,186 A | 11/1992 | Tsuru et al. | |
| 5,181,918 A | 1/1993 | Brandhorst et al. | |
| 5,344,417 A | 9/1994 | Wadsworth, Jr. | |
| 5,425,770 A | 6/1995 | Piez et al. | |
| 5,496,284 A * | 3/1996 | Waldenburg | 604/191 |
| 5,529,463 A * | 6/1996 | Layer et al. | 417/403 |
| 5,531,255 A | 7/1996 | Vacca | |
| 5,531,683 A * | 7/1996 | Kriesel et al. | 604/89 |
| 5,549,380 A | 8/1996 | Lidgren | |
| 5,755,787 A | 5/1998 | Camprasse et al. | |
| 5,772,665 A | 6/1998 | Glad et al. | |
| 5,842,786 A | 12/1998 | Solomon | |
| 5,846,484 A | 12/1998 | Scarborough | |
| 5,876,452 A | 3/1999 | Athanssiou et al. | |
| 6,007,521 A * | 12/1999 | Bidwell et al. | 604/264 |
| 6,027,742 A | 2/2000 | Lee et al. | |
| 6,049,026 A | 4/2000 | Muschler | |
| 6,123,236 A | 9/2000 | Bloom | |
| 6,143,293 A | 11/2000 | Weiss et al. | |
| 6,383,190 B1 | 5/2002 | Preissman | |
| 6,409,708 B1 | 6/2002 | Wessman | |
| 6,682,347 B2 * | 1/2004 | Aoyagi et al. | 433/90 |
| 6,709,149 B1 | 3/2004 | Tepic | |
| 6,736,799 B1 | 5/2004 | Erbe et al. | |
| 6,796,957 B2 * | 9/2004 | Carpenter et al. | 604/93.01 |
| 6,887,272 B2 | 5/2005 | Shinomlya et al. | |
| 7,445,633 B2 | 11/2008 | Hoerger et al. | |
| 2004/0226894 A1 * | 11/2004 | Okazaki | 210/756 |
| 2004/0254538 A1 | 12/2004 | Murphy et al. | |
| 2004/0267201 A1 * | 12/2004 | Agerup | 604/152 |
| 2005/0074433 A1 | 4/2005 | Stoll | |
| 2006/0153001 A1 | 7/2006 | Hoerger et al. | |
| 2007/0221742 A1 | 9/2007 | Hoerger et al. | |
| 2009/0022878 A1 | 1/2009 | Hoerger et al. | |

FOREIGN PATENT DOCUMENTS

| | | |
|---|---|---|
| DE | 3834944 | 4/1990 |
| DE | 4141129 | 6/1993 |
| EP | 0361896 A2 | 4/1990 |
| EP | 0361896 A3 | 1/1991 |
| EP | 0470393 A1 | 2/1992 |
| EP | 0739631 A2 | 10/1996 |
| EP | 0761896 A1 | 3/1997 |
| EP | 1230942 A2 | 8/2002 |
| FR | 2815021 A1 | 4/2002 |
| JP | 60-142857 | 7/1985 |
| JP | S61226055 A | 10/1986 |
| JP | 03-085179 | 4/1991 |
| JP | H04244164 | 1/1992 |
| JP | 04-221538 | 8/1992 |
| JP | H05305134 | 11/1993 |
| JP | 07-313586 | 12/1995 |
| JP | 08-024347 | 1/1996 |
| JP | H08503157 A | 4/1996 |
| JP | 09-201330 | 8/1997 |
| JP | 2000508911 A | 7/2000 |
| JP | 2001137328 A | 5/2001 |
| JP | 2003010301 | 1/2003 |
| WO | 97/46202 A1 | 12/1997 |
| WO | 9959500 | 11/1999 |
| WO | 00/45867 A1 | 8/2000 |
| WO | WO-01/32100 A2 | 5/2001 |
| WO | 02/15950 A1 | 2/2002 |
| WO | 02/068010 A1 | 9/2002 |
| WO | 2005/014068 A1 | 2/2005 |

OTHER PUBLICATIONS

"Written Opinion of the International Searching Authority for Application No. PCT/US2006/41202, date mailed Sep. 26, 2007", 7 pgs.

"European Patent Application No. 04750971.6, Communication mailed Jun. 12, 2008", 5 pgs.

"International Application Serial No. PCT/US06/41202, International Preliminary Report on Patentability mailed Sep. 3, 2008", 10 pgs.

"International Application Serial No. PCT/US06/41202, International Search Report mailed Sep. 26, 2007", 3 pgs.

"International Application Serial No. PCT/US06/41202, Written Opinion mailed Sep. 26, 2007", 7 pgs.

"Japanese Application No. 2002-506661, Notice of the Reason for the Rejection mailed Feb. 27, 2008", (w/ English Translation), 7 pgs.

"Japanese Application No. 2002-506661, Official Notice of Reason for the Final Rejection mailed Jul. 11, 2008", (w/ English Translation), 4 pgs.

Kaneko, Y., et al., "Synthesis and Swelling—deswelling kinetics of poly(N-isopropylacrylamide) hydrogels grafted with LCST modulated polymers", *Journal of Biomaterials Science, Polymer Edition*, 10(11), (1999), 1079-1091.

Stile, R. A., et al., "Synthesis and Characterization of Injectable Poly(N-isopropylacrylamide)-Based Hydrogels That Support Tissue Formation in Vitro", *Macromolecules*, 32, (1999), 7370-7379.

Taiwan patent application No. 94113414, English Translation of an Office action dated Jul. 22, 2011 (5 pages).

Taiwan patent application No. 94113414, Taiwanese version of the Office action dated Jul. 22, 2011 (12 pages).

Japanese Office Action dated Sep. 13, 2011 from corresponding Japanese Application No. 2002-520871 with English Translation.

"International Application Serial No. PCT/CH2004/000335, Written Opinion mailed Feb. 9, 2005," (with English translation), 10 pages.

"International Application Serial No. PCT/CH2004/000335, International Search Report mailed Feb. 9, 2005," (with English translation), 6 pages.

U.S. Appl. No. 12/242,207, Response filed Nov. 3, 2009 to Non Final Office Action mailed May 4, 2009.

U.S. Appl. No. 12/242,207, Office Action mailed May 4, 2009.

Canada Application Serial No. 2,419,850, Office Action mailed Jul. 7, 2009.

International Patent Application Serial No. PCT/CH01/00494, International Preliminary Examination Report dated Aug. 26, 2002, (w/ English Translation).

International Patent Application Serial No. PCT/CH01/00494, International Search Report mailed Dec. 5, 2001, (w/ English Translation).

International Search Report for Application No. PCT/CH03/00537, date mailed Apr. 16, 2004.

U.S. Appl. No. 11/349,693, Response filed Jun. 16, 2008 to Final Office Action mailed Mar. 17, 2008.

U.S. Appl. No. 11/349,693, Notice of Allowance mailed Jun. 30, 2008, NOAR.

U.S. Appl. No. 11/349,693, Final Office Action mailed Mar. 17, 2008, FOAR.

U.S. Appl. No. 11/349,693, Non-Final Office Action Mailed Sep. 7, 2007.

U.S. Appl. No. 11/349,693, Response filed Dec. 7, 2007 to Office Action mailed Sep. 7, 2007.

Merriam-Webster MedLine Plus Online Medical Dictionary definitions of "vacuum," "membrane," and "septum." Accessed online at <http://www.nlm.nih.gov/medlineplus/mplusdictionary.html> on Oct. 16, 2008.

Definition of "membrane." The American Heritage Dictionary of the English Language, Fourth Edition Copyright 2007, 2000 by Houghton Mifflin Company. Updated in 2007.

"Body." in: Costell, RB, ed., Random House Webster's College Dictionary (1991 ed.), p. 152.

(56) References Cited

OTHER PUBLICATIONS

Medline Plus Medical Dictionary Definition of "osteogenic." Accessed online Dec. 12, 2005.
Dictionary.com definition of "mesenchymal." Accessed online Dec. 12, 2005.
EPOline Online Public File Inspection entry for WIPO document WO2000CH00443, accessed online Dec. 13, 2005.
Linkart TA et al., 1996, Growth factors for bone growth and repair: IGF; TGF beta, and BMP. Bone 19 (1 Suppl): 1S-12S. Abstract only.
U.S. Appl. No. 10/370,606, Non-Final Office Action mailed Dec. 19, 2005.
U.S. Appl. No. 10/370,606, Final Office Action mailed May 31, 2006.
U.S. Appl. No. 10/370,606, Non-Final Office Action mailed Dec. 18, 2006.
U.S. Appl. No. 10/370,606, Final Office Action mailed Jun. 15, 2007.
U.S. Appl. No. 10/370,606, Non-Final Office Action mailed Dec. 11, 2007.
U.S. Appl. No. 10/370,606, Final Office Action mailed May 1, 2008.
U.S. Appl. No. 10/370,606, Non-Final Office Action mailed Oct. 31, 2008.
U.S. Appl. No. 10/370,606, Final Office Action mailed May 21, 2009.
U.S. Appl. No. 10/370,606, Non-Final Office Action mailed Dec. 16, 2009.
U.S. Appl. No. 10/370,606, Final Office Action mailed Jun. 3, 2010.
Barry T. Mitzner, Hematology Methods for the Office Laboratory Power Point Presentation, Jun. 12, 1999.
European Patent Application No. 04750971.6, Communication mailed Jun. 12, 2008.

\* cited by examiner

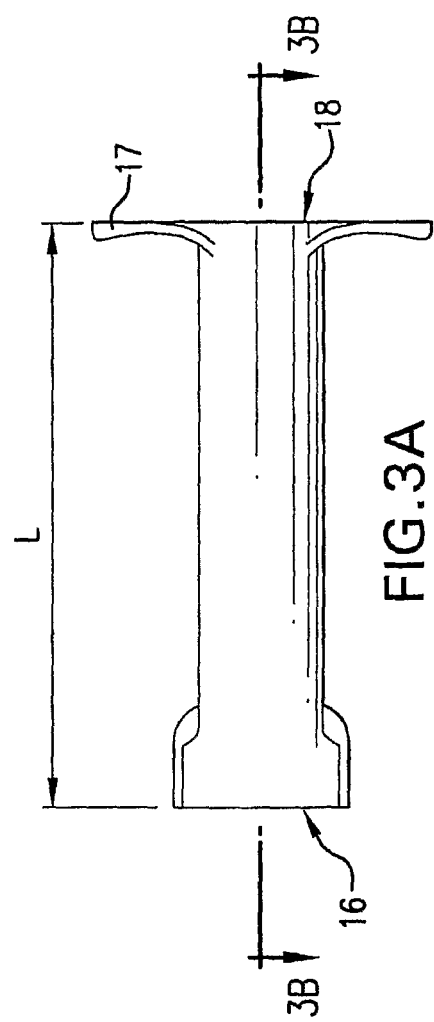
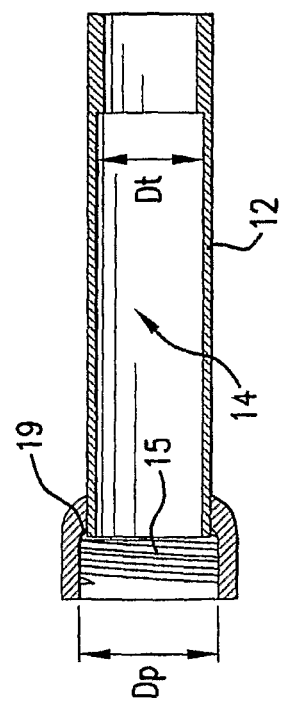
FIG.3A
FIG.3B

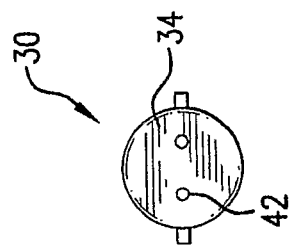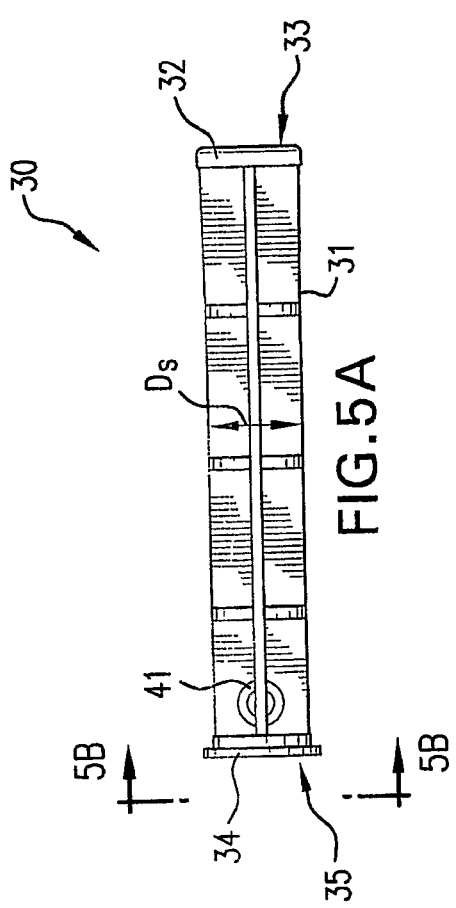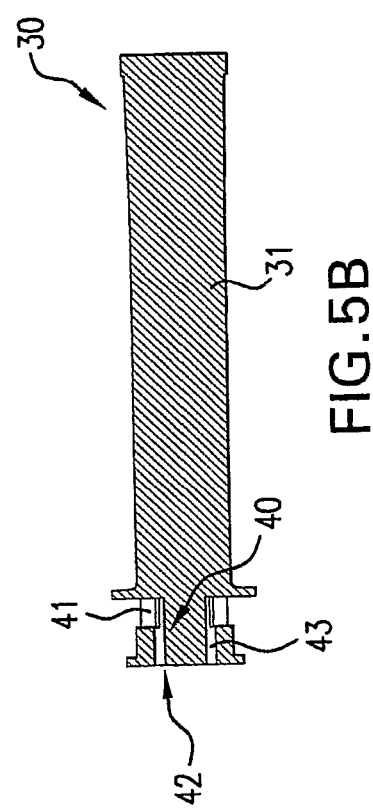

PERFUSION DEVICE AND METHOD

RELATED APPLICATIONS

This application is a U.S. National Stage Filing under 35 U.S.C. 371 from International Patent Application Ser. No. PCT/US2006/041202, filed Oct. 19, 2006, and published on Apr. 26, 2007 as WO 2007/048016 A2 and republished as WO 2007/048016 A3, which claims the priority benefit of U.S. Provisional Application Ser. No. 60/729,167, filed Oct. 20, 2005, the contents of which are incorporated herein by reference in their entirety.

FIELD OF THE INVENTION

The present invention relates to bone repair, and more particularly to an improved device and method for perfusing an implantable bone graft biomaterial with a liquid or fluid.

Gaps or voids in bone may be caused by trauma, disease, birth deformities, or other causes. In order to repair these voids, surgical procedures are used to implant biologically compatible bone graft materials into the voids. A biomaterial is broadly defined herein as any material that is compatible with in-vivo implantation. Biomaterials may include organic materials such as bone or non-organic and synthetic materials including various mineral compositions, polymers, ceramics, or other materials. The biomaterials may come in numerous forms, including pastes and cements, powders, pellets, granules, or formed geometric and other shapes. Biomaterials used in bone repair may be non-porous or porous in structure.

One type of porous biomaterial that may be used for bone grafts includes osteoconductive materials that promote new bone formation by providing a structure or scaffold that supports the new bone growth. Bone graft repair materials may beneficially include mixing such a porous biomaterial with a biological fluid derived from the bone graft recipient that induces bone growth such as blood, bone morphogenic protein (BMP) suspension, bone marrow aspirate (BMA), or other similar fluids. These fluids provide the proteins and other raw materials needed to induce new bone growth. Bone marrow aspirate, essentially enriched blood which may be harvested from the patient's iliac crest using an extraction syringe, is one such favored biological fluid that has been found to increase the efficacy of bone grafts. The biological fluids also tend to somewhat thicken and congeal the biomaterial-fluid mixture to facilitate delivery of the bone graft materials to the implantation site and keep them in place.

Known techniques of perfusing porous biomaterials with blood, bone marrow aspirate or another fluid may sometimes result in less than optimal saturation or impregnation of the biomaterial. These techniques may include mixing the biomaterial and fluid in an open sterile bowl, or filling a mixing tube containing the biomaterial with a fluid. In the latter technique, the fluid may be injected from a medical extraction syringe into one end of the mixing tube causing the fluid to flow under a slightly positive pressure through the biomaterial. In some devices, a vent and filter may be provided at an opposite of the mixing tube to expel air trapped between the biomaterial particles. Typically after the fluid is mixed with the biomaterial in either of the foregoing known techniques, the user must sometimes wait a period of time to allow the fluid to seep into the porous substance. This wastes precious time during the surgical procedure which optimally should be kept as short as possible. Also, the bone marrow aspirate or other fluid that may be used may also not thoroughly mix with the biomaterial nor infiltrate adequately into the pores of the biomaterial, resulting in less than ideal saturation of the biomaterial with the aspirate. This can compromise the efficacy of the bone graft. In addition, the biomaterial and fluid mixture may not be directly deliverable to the bone repair site. Therefore, an intermediate step may be required that involves expelling the mixture into a sterile bowl, and then implanting the mixture by hand into the bone void.

Accordingly, there is a need for a device and method for perfusing biomaterials with bone marrow aspirate or other fluid desired in a surgical procedure that provides improved saturation of the biomaterial and in a less amount of time. There also is a further need for a device that allows the biomaterial and fluid mixture to be directly delivered from the perfusion device into the bone repair site.

SUMMARY OF THE INVENTION

The invention is generally directed to an improved device and method for perfusing a biomaterial with a fluid, such as but not limited to bone marrow aspirate. According to one aspect of the invention, a perfusion device is provided that allows a negative pressure or vacuum to be applied to the biomaterial-fluid mixture. The vacuum advantageously provides superior perfusion of the fluid into the pores of the biomaterial and thorough saturation, in contrast to known techniques. Applying a vacuum to the biomaterial-fluid mixture also advantageously reduces the time required for satisfactory saturation of the biomaterial with the fluid, thereby saving surgical time. In addition, the perfusion device described herein optionally permits direct delivery of the biomaterial-fluid mixture into the bone repair implantation site from the mixing container.

According to one embodiment, a perfusion device includes a container having an internal chamber configured for holding a biomaterial. The perfusion device preferably has at least one end including an inlet port for introducing a liquid or fluid, such as bone marrow aspirate, blood, antibiotics, etc. In one possible embodiment, the inlet end of the perfusion device is preferably configured to connect directly to a medical syringe via a standard Luer port and fitting commonly used in the art. The liquid contents within the medical syringe may then be injected or pumped into the internal chamber of the perfusion device holding the biomaterial implant.

In some embodiments, the container preferably includes a vent for releasing trapped air or gas from the biomaterial chamber. A means for preventing the release of liquid or fluid through the container vent is preferably provided. In some embodiments, the liquid release prevention means may be a flow control device such as a filter or a vent plug that allows only air or gas to pass, but prevents liquid from passing therethrough.

In a preferred embodiment, the container includes a means for sealing or blocking the air and gas vent to allow a vacuum to be drawn on the biomaterial chamber for perfusing the biomaterial with the injected liquid. Preferably, the sealing or blocking means prevents the flow of air/or gas from being pulled into the biomaterial chamber of the container from atmosphere when a vacuum is applied to the chamber. In one possible embodiment, a self-sealing vent plug may be provided that allows air and gas to pass through (desired when the biomaterial chamber is first being pumped full of liquid), but which becomes solid or plugged once it is contacted by the liquid. In the solid condition, neither liquid nor air or gas can pass through the self-sealing vent plug in either direction. Advantageously, the self-sealing vent plug performs a dual function of both the liquid release preventing means and the vent sealing/blocking means which reduces the number of components required and costs. In other embodiments, the vent sealing/blocking means may be provided by a one-way flow valve or hydrophobic venting material.

In some embodiments, the perfusion container may be rigid in structure, such as a plastic syringe tube for example. A removable cap may be provided and unfastened to allow access to the biomaterial within. In other embodiments, the perfusion container may have a pliable and flexible structure, such as a flexible container which in some embodiments may be a plastic bag for example. Access to the biomaterial may be provided by tearing the container.

The biomaterial used with the perfusion device described herein may be any porous or non-porous organic material or inorganic or synthetic material in any form, shape, or size as described herein. In some embodiments of the invention, the syringe can be filed with a bone graft material, such as a synthetic bone graft material. Examples of suitable bone graft materials include a calcium phosphate cancellous bone substitute, such as ChronOS™ (r) (available from Synthes, Inc. of West Chester, Pa.), Vitoss® (r) (available from Orthovita of Malvern, Pa.), or Conduit™ (r) (available, from DePuy, Inc. of Raynham, Mass.). In one possible embodiment, the bone graft material may be particulate or granular in form. In another possible embodiment, the bone graft material may be shaped as a strip. Other suitable shapes and forms of bone graft material may be used and the invention is not limited to those disclosed herein.

Other materials that are capable of liquid absorption may be used according to principles of the present invention, which is not limited to the either the medical field or bone replacement indications. Although the preferred embodiments and method described herein are most beneficial for perfusing a fluid into a porous material, non-porous materials may be used where quick and thorough saturation are desired. Accordingly, the invention is not limited to use with porous materials alone.

The chamber could also contain materials to enhance the fluid such as adsorptive media to remove unwanted constituents from the fluid such as excess water, specific cell types or specific proteins. It could be used to reconstitute lyophilized biomaterials or biomaterial coatings such as demineralized bone or therapeutic agents such as bone morphogenic proteins. In certain embodiments, the materials to be perfused into the biomaterial can include antibiotics, analgesics, growth factors, bone marrow aspirates, peptides, cell suspensions, water for rehyrdryation, antiseptics, clotting agents, blood, saline solution, proteins, materials to enhance handling properties (such as hyrdrogels and hylauronic acid), therapeutic agents, etc.

According to one embodiment, a device for perfusing a material with a liquid includes a container having a first internal chamber configured to hold the material; a port for introducing the liquid into the chamber; a vent for releasing gas and liquid from the chamber; and a means for sealing the vent to allow a vacuum to be drawn on the first chamber. In one embodiment, the means for sealing the vent is a one-directional flow valve. In another embodiment, the means for sealing the vent is a self-sealing plug that is porous to gas but forms a solid seal when contacted by the liquid. In some embodiment, the container is rigid or flexible. In one embodiment, the container is a syringe including a movable plunger. The syringe may include a proximal vent and a distal vent. In other embodiments, the container includes a second internal overflow chamber connected to the first internal chamber so that gas and liquid can flow from the first chamber to the second chamber. The second chamber may be connected via the vent to the first chamber in a preferred embodiment. The perfusion device may further include a vacuum apparatus releasably coupled to the container for drawing a vacuum on the first internal chamber. In one embodiment, the vacuum apparatus is a medical syringe, which in some embodiments may also be used to extract the liquid from a patient (e.g., bone marrow aspirate) and inject the liquid into the perfusion device.

According to another embodiment, perfusion device includes a tubular body having a proximal end, a distal end, and an internal chamber configured to hold a biomaterial; a plunger movable within the chamber; a port at one end of the body for introducing a liquid into the chamber; a chamber vent for releasing gas and liquid from the chamber; and a flow control device for sealing the vent to allow a vacuum to be drawn on the container. In one embodiment, the flow control device is selected from the group consisting of a one-way flow valve and a self-sealing plug. In another embodiment, the perfusion device further includes an end cap to close the distal end of the tubular body. The end cap and plunger may each have a vent for releasing gas and liquid from the proximal and distal ends of the chamber in some embodiments. In one embodiment, the vent is disposed in the plunger. According to another aspect of the invention, the plunger may be hollow and includes an overflow cavity in fluid communication with the internal chamber via the vent for receiving gas and liquid. In the hollow plunger embodiment, and in other embodiments of the perfusion device, the flow control device is a resilient on-way flow valve preferably disposed in or connected to the vent.

According to another aspect of the invention, a perfusion system for material includes (a) a container having an internal chamber configured to hold a material, the container including a port for introducing a liquid into the container to contact the material; a chamber vent in fluid communication with the chamber, the vent including a flow control device operable to allow the passage of gas or liquid in one direction from the chamber and further operable to prevent the passage of gas or liquid in an opposite direction into the chamber; and (b) a vacuum apparatus removably connected to the container and operable to draw a vacuum on the chamber of the container. In one embodiment, the flow control device is selected from the group consisting of a one-way flow valve and a self-sealing plug. In another embodiment, the vacuum apparatus is a medical syringe removably coupled to the container. In one embodiment, the container is a perfusion syringe. The perfusion syringe includes a plunger movable within the syringe. In some embodiments, at least part of the chamber vent being formed by a venting passageway through the plunger. The perfusion syringe in some embodiments may include an end cap having a venting passageway forming part of the chamber vent. In some embodiments, the container may be flexible. In other embodiments, the container further includes a second overflow chamber in fluid communication with the internal chamber for receiving gas and liquid from the internal chamber. The second overflow chamber may be connected to the internal chamber via the vent.

A method of perfusing a material with a liquid or fluid is also provided. The method generally includes providing a container filled with a material, injecting a fluid (e.g., a liquid) into the container to contact the material, and applying a vacuum to the container to perfuse the material with the liquid.

In another embodiment, a method of perfusing a material with a liquid, may include the steps of providing a container defining an internal chamber and a material disposed in the container; delivering a liquid into the container; contacting the material with the liquid; stopping delivery of the liquid into the container; and drawing a vacuum on the container to perfuse the material with the liquid. In a preferred embodiment, the vacuum is drawn at a constant container volume. In the same or other embodiments, the vacuum is preferably drawn without disturbing the material. In another embodiment, the delivering step includes coupling a medical syringe holding the liquid to the container and injecting the liquid into the container from the medical syringe. In one embodiment, the same medical syringe is used to draw the vacuum on the container. The method may further include the step of venting air or gas from the container through a vent concurrent with the liquid delivering step. In other embodiments, the method further includes the step of sealing the vent concurrent with the vacuum drawing step. In one embodiment, the container is a perfusion syringe. The perfusion syringe preferably includes a plunger having a sealing plate to seal one end of the syringe. In one embodiment, the plunger sealing plate is not moved during the vacuum drawing step to allow the vacuum to be drawn at a constant container volume.

As the term is used herein, it will be understood that gas is a broad term and includes air which is a gas.

These foregoing and other features and advantages of the present invention will become apparent from the remainder of the disclosure, in particular the following detailed description of the preferred embodiments, all of which illustrate by way of example the principles of the invention.

DETAILED DESCRIPTION OF THE PREFERRED EMBODIMENTS

The features of the preferred embodiments will be described with reference to the following drawings where like elements are labeled similarly, and in which:

FIGS. 3A and 3B show a side view and a longitudinal cross-sectional view therethrough, respectively, of the perfusion syringe body of FIG. 1;

FIGS. 5A and 5B show a side view and a longitudinal cross-sectional view therethrough, respectively, of the perfusion syringe plunger of FIG. 1;

FIG. 5C shows an end view of the plunger of FIGS. 4A and 4B taken in the direction of line 5C-5C in FIG. 5A;

DETAILED DESCRIPTION OF THE PREFERRED EMBODIMENTS

Figure 1:
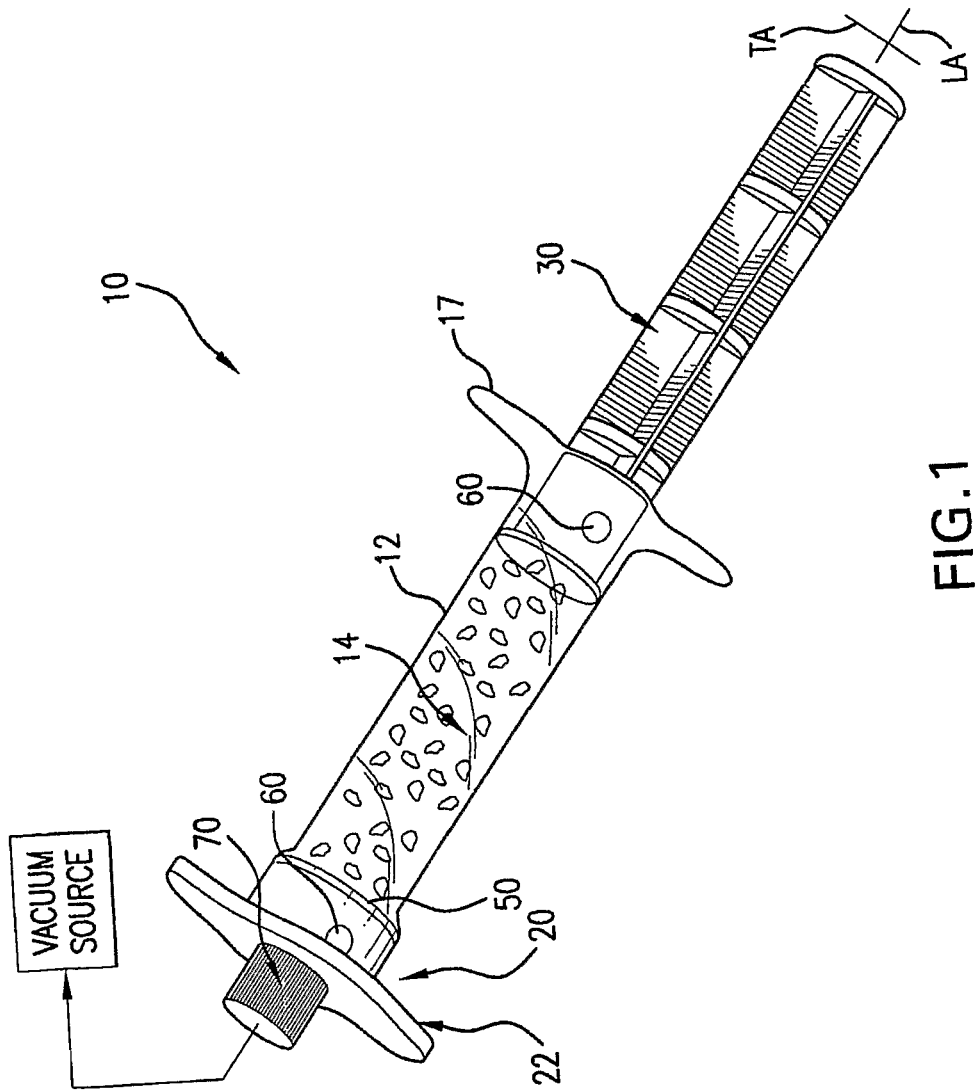
FIG. 1 is a perspective view of a preferred embodiment of a perfusion container in the form of a syringe having a biomaterial chamber.
Figures 2A, 2B:
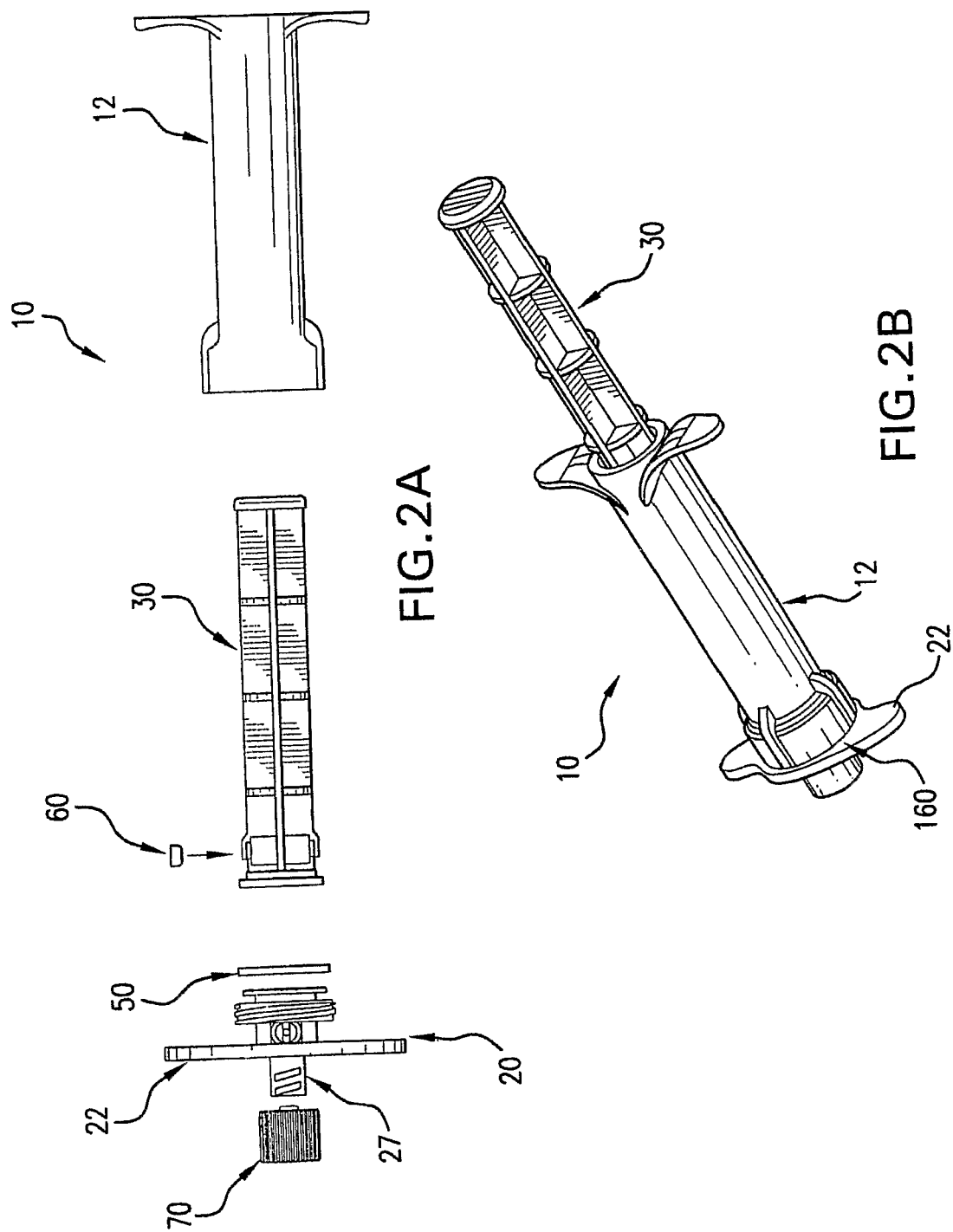
FIG. 2A shows an exploded view of the components of the perfusion syringe of FIG. 1.
FIG. 2B shows an additional perspective view of the perfusion syringe body of FIG. 1 from a different angle.

In order that the invention may be understood, preferred embodiments which are given by way of example only, will now be described with reference to the appended drawings. Accordingly, the preferred embodiments are described for convenience of reference and without limitation of the invention to embodiments described herein. The scope of the invention being defined by the claims appended hereto.

In one embodiment shown in FIGS. 1-5, a rigid-type perfusion device may be a container in the form of a perfusion syringe 10 having tubular body 12 having a distal end 16 and a proximal end 18. Body 12 defines an internal chamber 14 having a diameter "Dt" for holding a material, preferably a biomaterial in one embodiment. The body 12 further defines a longitudinal axis "LA" along the centerline and length "L" (FIG. 3) of the body and transverse axis "TA" defined perpendicular to the longitudinal axis. In one embodiment, the syringe body 12 preferably includes a finger flange 17 on end 18 for grasping and a threaded female connection 15 on opposite end 16 complementary configured and sized to receive a male-threaded syringe cap 20. The threaded end 16 of the syringe body 12 may be radially enlarged as shown in contrast to the rest of the main body to accommodate a syringe cap 20 having a threaded diameter larger than the main body of the syringe in one embodiment. Preferably, the two ends 16, 18 are open with one opening in end 16 configured for receiving the syringe end cap 20 and the other opening in opposite end 18 configured to receive at least part of a plunger 30 therethrough. The syringe body 12 is preferably made of plastic suitable for medical usage, such as polypropylene in one embodiment. However, other suitable plastics may be used. Other parts of the syringe 10 and exemplary illustrative dimensions are shown and described in herein.

The perfusion syringe 10 further includes a plunger 30, which may be one piece or construction from multiple pieces connected together (see FIGS. 5A-5C). The plunger 30 includes an elongated stem 31 with a thumb rest 32 at one end 33 and a sealing plate 34 at an opposite end 35. The plunger 30 is preferably sized and configured to complement the size and configuration internal chamber of the syringe body to be slidably received therein. The sealing plate 34 is preferably sized in cooperation with the diameter Dt of the internal syringe chamber to provide a generally leak-proof, yet slidable seal between the plunger 30 and syringe body 12. In a preferred embodiment, the sealing end 35 of the plunger 30 includes a vent 40 defining an internal venting passageway 43, which creates fluid communication with the internal chamber 14 of syringe 10. In one embodiment, vent 40 further includes at least one vent plug opening 41 configured to receive a self-sealing vent plug. Preferably, two vent plug openings 41 are provided on diametrically opposite sides of the plunger as shown. The vent plug openings 41 are preferably disposed and oriented transversely in the plunger 30. In one embodiment, the vent plug openings 41 are shown as being separate in a preferred embodiment and each extends only partially radially inwards towards each other without connecting. In another embodiment, a single transverse vent plug opening 41 extending completely and transversely through the plunger 30 may alternatively be provided (not shown).

In one embodiment, each plunger vent plug opening 41 may be connected to a corresponding hole 42 in the face of the sealing plate 34 by an internal venting passageway 43 as shown in the Figures. Each venting passageway 43 penetrates completely through the sealing plate and extends axially from the face of the sealing plate 34 to intersect the vent plug opening 41. The venting passageways 43 and vent plug openings 41 provide a means for allowing gas and air to be expelled from the syringe internal chamber 14 to atmosphere or secondary containments in some embodiments described herein. Preferably, the outside diameter Ds of the plunger stem 31 is sized slightly smaller than the diameter Dt of the syringe internal chamber 14 to provide a gap or passageway between the plunger and syringe body for the expelled air and gas to escape to atmosphere outside the syringe body. Concomitantly, the portion of the plunger 30 containing the two end plug openings 41 is also slightly smaller in diametrical dimension than the inside diameter of the syringe internal chamber 14 for the same purpose.

The plunger 30 is preferably made of plastic suitable for medical usage, such as high density polyethylene (HDPE). However, other suitable plastics may be used.

Figure 4C:
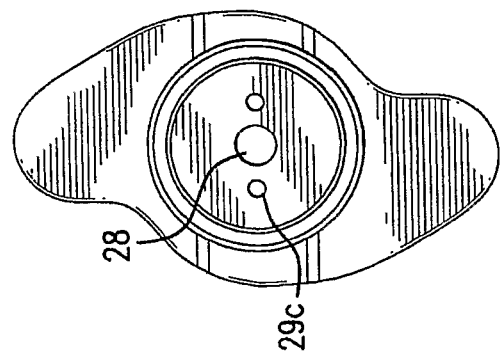
FIG. 4C shows an end view of the end cap of FIGS. 4A and 4B taken in the direction of line 4C-4C in FIG. 4A.
Figure 4B:
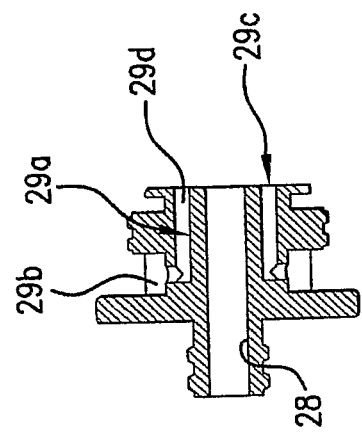
FIGS. 4A and 4B show a side view and a longitudinal cross-sectional view therethrough, respectively, of the perfusion syringe end cap of FIG. 1.
Figure 4A:
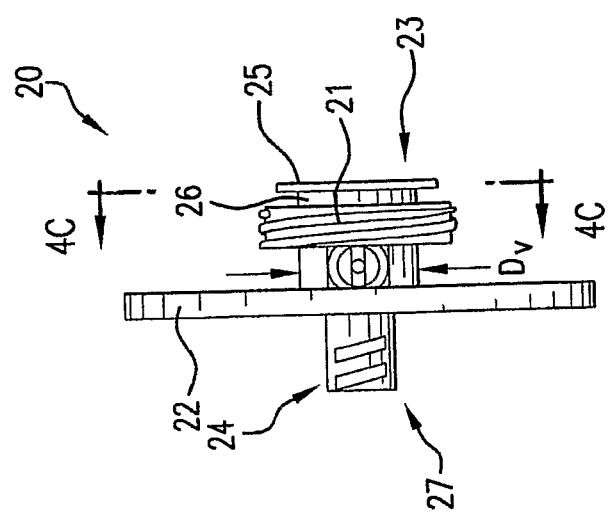

With continuing reference to FIGS. 1-5, and in particular FIGS. 4A-4C, the perfusion syringe 10 further includes a removable syringe cap 20 that attaches to the syringe body 12 and allows access to the biomaterial contained therein. In one embodiment, a syringe cap 20 has male threading 21 configured to mate with the female threading 15 of the syringe body 12 as described herein. Alternatively, in one embodiment, a quick disconnect cap may be provided that allows the cap to be removed with a quarter turn by the user (see e.g., FIG. 9). It will be appreciated that the cap 20 may be releaseably attached to the syringe body by other non-threaded means known in the art, such as a press-fit or friction-fit connection, etc. Accordingly, the invention is not limited to threaded syringe caps.

Figure 6:
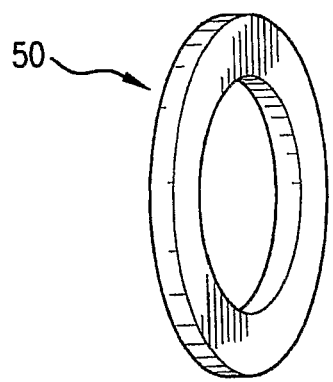
FIG. 6 shows a perspective view of a gasket useable with the syringe end cap of FIGS. 4A-C.

In one embodiment, the syringe cap 20 further includes a cap flange 22 for easy grasping to facilitate removal of the cap from the syringe body 12. In one embodiment, the syringe cap 20 has a sealing end 23 and an opposite coupling end 24 for coupling a medical syringe thereto. In one embodiment, the sealing end 23 of the syringe cap 20 has a sealing plate 25 which closes off one end of the perfusion syringe body 12 as shown in the Figures. In one embodiment, the sealing end 23 further contains an annular groove 26 configured to hold an O-ring spring gasket 50 (see FIG. 6). In this embodiment, the gasket 50 is complementary designed to mate with and be compressed against an annular seat 19 provided in the syringe body 12 (see FIG. 3B) when the syringe cap 20 is fully screwed into the body. The gasket 50 provides a seal on one end of the syringe body 12 in conjunction with the cap sealing plate 25 to prevent fluid leakage outwards from the syringe. The other end of the syringe body 12 is sealed by the sealing plate 34 of the plunger 30 as described herein. In one embodiment, the gasket 50 is preferably made of a material suitable for medical usage, such as a thermoplastic elastomer (TPE) such as Santoprene™. However, other suitable TPE's or sealing materials may be used.

The coupling end 24 of the syringe cap 20 opposite the sealing end 23 preferably includes a nipple 27 configured with a threaded Luer-type male fitting to receive and mate with a similarly configured female Luer-type fitting on a medical syringe containing the fluid to be transferred to the perfusion syringe 10 for impregnating the biomaterial. In one embodiment, a fluid delivery port 28 in the form of a round bore extends completely through the syringe cap 20 from one end 24 (e.g., through the nipple) to the opposite other end 23 (e.g., through the sealing plate). Fluid from the medical syringe is pumped through the fluid port into perfusion syringe. The fluid delivery port 28 also serves as a connecting point for a vacuum source to be coupled to syringe 10, as described herein.

Similar to the plunger 30, the syringe cap 20 includes a vent 29a, which in one embodiment includes at least one vent plug opening 29b that is configured to receive a vent plug and is transversely positioned in the cap. Preferably, two vent plug openings 29b are provided on diametrically opposite sides of the syringe cap 20. Each vent plug opening 29b is connected to a hole 29c in the face of the sealing plate 25 via an internal venting passageway 29d as shown. The venting passageways 29d internally bridges the threaded portion of the syringe cap from the sealing pressure/vacuum side of the threads to the side exposed to atmospheric pressure. The venting passageways 29d and vent plug openings 29b provide a means for allowing gas and air to be expelled from the syringe internal chamber 14 to atmosphere as the perfusion syringe 10 is being filled with fluid from the medical syringe. Accordingly, internal venting passageway 29d creates fluid communication between atmosphere and the internal chamber 14 of syringe 10. Preferably, the portion of the syringe cap 20 containing the two end plug openings 29b is slightly smaller in diametrical outside dimension Dv than the inside diameter Dp of the threaded end 16 of the syringe body 12 to provide a pathway for the air and gas to escape to atmosphere. Preferably, the syringe cap 20 is designed so that the inboard side of the cap flange 22 closest the syringe body does not completely contact the end of the syringe body when the cap is fully screwed into the body. This provides a small gap 160 (see FIG. 2B) which completes the path to atmosphere for air and gas expelled from the perfusion syringe through the vent plug openings.

The syringe cap 20 is preferably made of plastic suitable for medical usage, such as high density polyethylene (HDPE). However, other suitable plastics may be used.

Figure 7A:
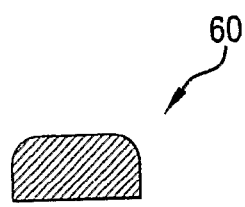
FIGS. 7A and 7B shows a perspective view and side view, respectively, useable with the perfusion syringe of FIG. 1.
Figure 7B:
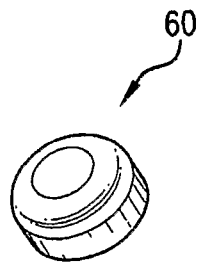

In a preferred embodiment, with reference to FIGS. 7A and 7B, filters or vent plugs 60 are provided that allow air and gas to escape to the atmosphere through the perfusion syringe vents as the biomaterial chamber is being filled with fluid or liquid. In one preferred embodiment, the filters or plugs 60, however, prevent the passage of fluid or liquid out from the syringe when all components are fully assembled (i.e., syringe body, cap, and plunger). The perfusion syringe 10 preferably includes a means for sealing or blocking the air and gas vents to allow a vacuum to be drawn on the biomaterial chamber for perfusing the biomaterial with the injected liquid. In a preferred embodiment, self-sealing vent plugs 60 of the type that swell and become solid upon contact with a liquid are provided to automatically form a solid seal that will not allow the passage of gas or liquid from either direction. Advantageously, these self-sealing vent plugs 60 perform a dual function of both preventing liquid release from the syringe vents and sealing/blocking the vents to allow a vacuum to be pulled on the biomaterial chamber. However, in some embodiments, separate components for providing the liquid release prevention function and vent sealing/blocking function may be provided.

Preferably, for economy of manufacture, the same size and type vent plugs 60 may be provided to fit in the vent plug openings 41, 29b respectively in both the syringe plunger and cap noted herein. In a preferred embodiment, the vent plug openings 41, 29b are circular in shape to accommodate round self-sealing vent plugs 60 as shown in FIGS. 7A and 7B. The self-sealing vent plugs are preferably made of a material suitable for medical usage, such as sintered ultra-high molecular weight polyethylene (UHMWPE) available from Micropore Plastics, Incorporated. However, other suitable vent plugs or filters may be used so long as they allow air and gas to escape while concomitantly preventing fluids from passing therethrough. In addition, other types of devices may be used to seal/block the vents in lieu of the self-sealing vent plugs so long as a tight seal to prevent air from being drawn into the perfusion syringe when the biomaterial is put under vacuum. Accordingly, in some other embodiments, the vent sealing/blocking function may be accomplished with a one-way valve such as a check valve or a hydrophobic venting material. Alternatively, the syringe may be structured to provide a manually-operated pivoting or slidable gate or door, or a removable cap, to open or close the syringe vents. Accordingly, the invention is not limited to the use of self-sealing vent plugs alone.

Figure 8:
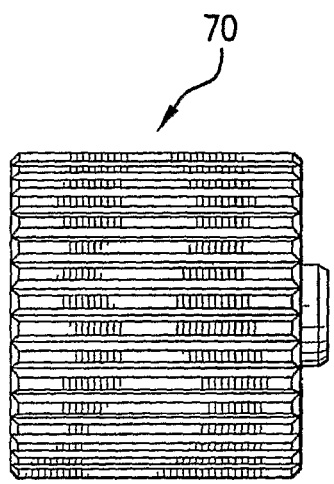
FIG. 8 shows a side views of the removable Luer cap useable with the perfusion syringe of FIG. 1.

The perfusion syringe 10 may include a Luer-type cap 70 (see FIG. 8) having female threads that are configured to mate with the Luer-type male threaded nipple 27 on the syringe cap 20. This provides a convenient means for closing and storing the perfusion syringe when not being filled with a fluid. The Luer cap 70 is preferably made of plastic suitable for medical usage, such as polypropylene (PP). However, other suitable plastics may be used.

The perfusion syringe 10 may be used and operates in the following manner. By way of example only, the use of bone marrow aspirate as the fluid will be described in one possible embodiment. However, it will be appreciated that other biological fluids may be used.

The process starts by providing a perfusion syringe 10 having an internal chamber 14 containing the desired biomaterial therein. By way of example only, a porous biomaterial such as synthetic calcium phosphate in granular form may be used as the biomaterial in one possible embodiment. The plunger 30 of the perfusion syringe 10 is positioned at least partially back in the syringe body to create a volumetric space in the internal chamber for holding the biomaterial. Preferably, the biomaterial is tightly packed in the syringe to eliminate the accumulation of excess air or gas in the chamber and prevent agitation of the biomaterial during the perfusion process. At this stage, air or gas is trapped both between adjacent granules or particles of biomaterial and within the porous individual granules or particles.

During the surgical bone repair procedure, bone marrow aspirate may be harvested from the patient's iliac crest using a medical extraction syringe (not shown) equipped with a needle on one end. Alternatively, other suitable biological fluids that facilitate new bone growth may be used. The medical syringe preferably has a Luer-type fitting where the needle is connected to the syringe. After the bone marrow aspirate is extracted from the patient, the needle is removed and the medical syringe is coupled to the threaded Luer-type nipple 27 on the cap 20 of the perfusion syringe 10.

The plunger on the medical syringe is pushed forward by the user to force the bone marrow aspirate to flow into the perfusion syringe and through the biomaterial. As the bone marrow aspirate continues to fill the perfusion syringe and contacts the biomaterial, any air or gas trapped between adjacent granules of or in the biomaterial in the perfusion syringe is forced preferably towards one or both ends of the perfusion syringe. Preferably, the position of the perfusion syringe plunger is not moved so that the fluid delivery and gas/air liberation step is performed at a constant volumetric capacity within syringe 10. This ensures that the fluid does not merely fill an increasing volume, but rather is used to effectively displace the air trapped between and within the biomaterial granules. The air or gas is expelled from the perfusion syringe to atmosphere through a syringe venting system, for example, as described herein. In one embodiment, the air or gas first passes from the syringe through the holes in the sealing plates of the syringe cap or plunger, then through the respective internal venting passageways, and finally out to atmosphere through the vent plugs in either end of the syringe.

Preferably, the coupled medical and perfusion syringes are held vertically when the bone marrow aspirate is forced through the perfusion syringe. This vertical alignment eliminates the formation of an air or gas pocket along a length of the perfusion syringe if the syringe were held horizontally. This also reduces the chance of residual gases or air being trapped in the biomaterial and ensures that any residual air or gases trapped in the perfusion syringe will efficiently accumulate in one end of the syringe for subsequent expulsion. In contrast to known perfusion mixing tubes, since the preferred embodiment shown in FIGS. 1-5 has a means for expelling air from either end of the perfusion syringe (e.g., venting passageways and vent plugs in the syringe cap and plunger), either the medical or perfusion syringe advantageously may be held in the top or bottom position without adversely affecting the saturation of the biomaterial or expulsion of gases from the perfusion syringe.

After the air or gases have been driven out of the syringe 10 and the liquid reaches the vent plugs, the vent plugs swell upon contact with the liquid and form a seal that will not allow passage of gas or liquid from either direction. This "sealing off" by the vent plug in turn creates a chamber 14 that is now capable of withstanding a negative pressure or vacuum.

With the perfusion syringe 10 having been filled with bone marrow aspirate and the trapped air or gases present between the biomaterial granules or particles has been expelled from the perfusion syringe, the user then applies a negative pressure or vacuum to the biomaterial chamber 14. Preferably, the vacuum is applied by conveniently using the medical syringe previously containing the bone marrow aspirate by pulling back the medical syringe plunger in a reverse direction. Alternatively, other means of providing a vacuum to the biomaterial chamber may be used such as but not limited to connecting a separate medical vacuum pump or similar mechanical or manual device to apply a vacuum to the perfusion syringe. Any remaining residual air or gas trapped within the pores of the biomaterial itself, now subjected to a vacuum, will expand outward and be released from the particles. This causes the surrounding bone marrow aspirate or other liquid to flow rapidly into the evacuated pores that are under negative pressure and become impregnated or perfused with the liquid. Advantageously, this micro-level expansion of air trapped in the pores of the biomaterial and accompanying micro-levels of perfusion both resulting from the vacuum provide superior infiltration of the bone marrow aspirate or other liquid into the biomaterial in contrast to known perfusion techniques. Also advantageously, the vacuum is also applied to the internal biomaterial chamber of the perfusion syringe without disturbing the biomaterial.

Increasing levels of vacuum have been found by the inventors to be associated with concomitantly higher levels of both liberating air trapped in the biomaterial pores and increased liquid perfusion. In one embodiment, the perfusion syringe preferably is capable of applying a vacuum or negative pressure to the biomaterial in the range of about −10 to −30 in. Hg. using the method described herein. More preferably, the vacuum applied may be in the range of about −25 in. Hg. to −30 in. Hg for optimal perfusion effectiveness. Because the perfusion device and method described herein first effectively drives off excess air trapped between the particles, application of the vacuum to the biomaterial is more efficient and productive. Advantageously, this permits the high levels of vacuum as described herein to be applied to the biomaterial using only the medical syringe and its short plunger stroke as the vacuum source. This result in greater liberation of air trapped within the pores of the biomaterial and more effective perfusion.

After the vacuum step is complete, the biomaterial bone graft saturated with bone marrow aspirate or other liquid advantageously is now ready for implantation. The present invention preferably significantly reduces or eliminates any of the operative procedure delays or "hold time" needed by known perfusion techniques to allow the fluid to seep into and saturate the biomaterial. In addition, these known techniques do not effectively liberate trapped air or gas from the pores of the biomaterial since they do not produce the micro-levels of air or gas expansion in the pores of the biomaterial as discussed herein and its concomitant benefits.

The bone marrow aspirate thickens and congeals the biomaterial. To implant the biomaterial in the bone repair site or void, the user next unscrews the end cap 20 from the perfusion syringe 10 and may inject the biomaterial directly into the repair site. Advantageously, in contrast to the prior art, an intermediate step is not necessary to first transfer the biomaterial to a container or bowl before manually implanting the biomaterial in the repair site.

Figure 9:
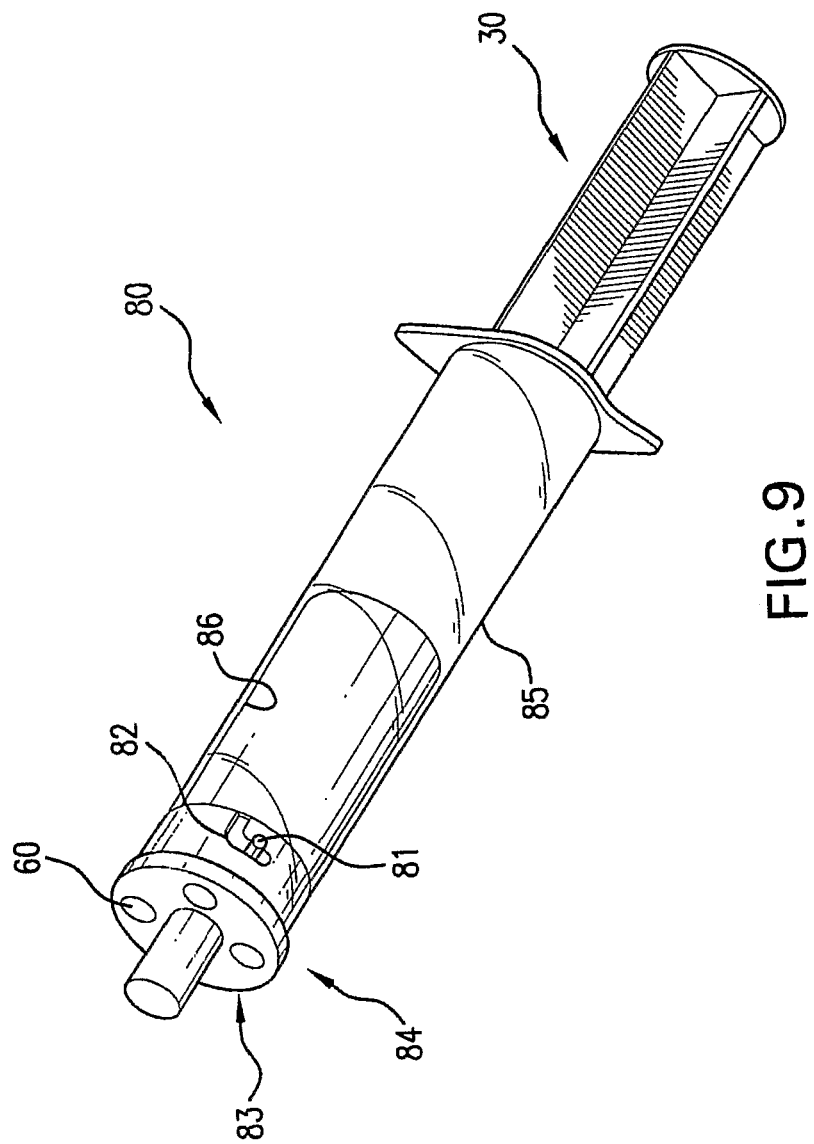
FIG. 9 shows a perspective view of an alternative embodiment of the perfusion syringe of FIG. 1 having a quick-disconnect type end cap.

FIG. 9 shows an alternative embodiment of a perfusion syringe 80 having slightly different syringe cap design. In this embodiment, the syringe 80 is provided with a quick disconnect cap 84 which may be removed by a quarter turn of the cap. A pin 81 and slot 82 quick disconnect is shown; however, any suitable design may be used so long as the cap to syringe body connection is tight and leak-proof. The syringe body 85 is complementary configured to accommodate the pin and slot arrangement of the cap 84. The biomaterial is disposed in internal chamber 86 of the syringe. In FIG. 9, the vent plugs 60 are preferably disposed in an axial end 83 of the cap 80. Preferably at least one vent plug 60 is provided in the syringe cap 80; however, a plurality of vent plugs may be used as shown. The syringe plunger 30 preferably is also provided with at least one vent plug 60 as in the previous plunger design described herein.

Figure 10A:
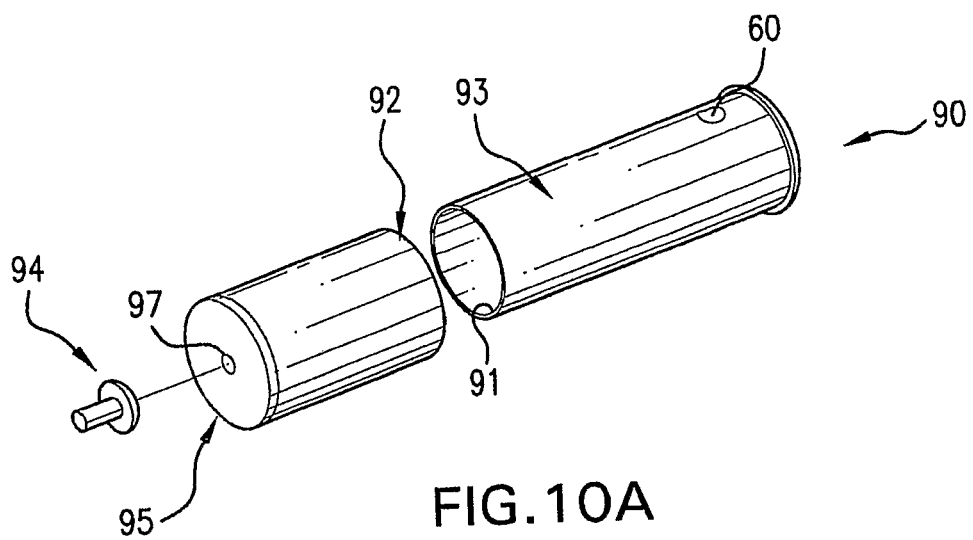
FIG. 10A shows a perspective view of an alternative embodiment of a plunger useable with the any of the foregoing perfusion syringes.
Figure 10B:
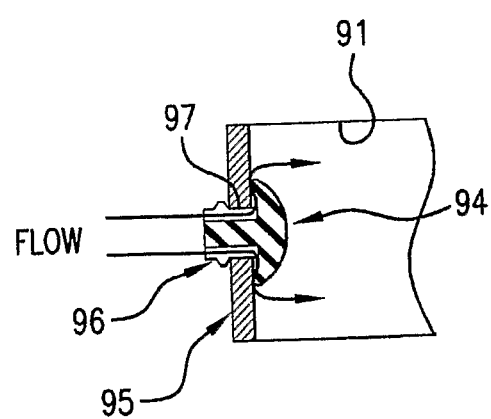
FIG. 10B shows a cross-sectional view through the plunger of FIG. 10A and shows a flow control device in the distal end of the plunger.

FIGS. 10A&B show an alternative embodiment of a hollow plunger which may be used with either of the foregoing perfusion syringes. The hollow plunger 90 has an internal cavity 91 that acts as a second chamber to collect any overflow of fluid and air or gas from the first or primary syringe internal chamber 14 containing the biomaterial. Accordingly, if the medical syringe contains more fluid than the primary biomaterial chamber can hold, the primary chamber may be overfilled and the excess fluid would accumulate in the second overflow chamber of the hollow plunger 90. The plunger 90 may be constructed of one or more pieces joined together. In one embodiment, the hollow plunger is made from two pieces 92, 93 that may be connected by press-fitting or any other suitable means.

With continuing reference to the hollow plunger of FIGS. 10A&B, in one embodiment, a one-way valve such as a check valve 94 or other flow control device connects the first and second chambers of the perfusion syringe 10 or 80 and plunger 90, respectively. As the fluid is pumped through the perfusion syringe, the excess fluid and gas or air may enter the plunger cavity through the one-way flow control device, which preferably is disposed in the sealing plate 95 of the plunger 90. Fluid or air/gas flow in a reverse direction from the plunger chamber (internal cavity 91) back into the primary syringe biomaterial chamber 14 (which in one example may be caused by pulling the vacuum on the primary chamber as described herein) is prevented by the one-way flow control device. In one embodiment, the valve may be a resilient commercially-available umbrella-style one-way valve available from Vernay Laboratories, Incorporated. In one embodiment, a valve seat 96 and aperture 97 are provided in the plunger sealing plate 95 that are configured to receive and attach the valve 94 to the plate. In one embodiment, the umbrella valve 94 has a stem and a concave umbrella-shaped head. The concave head is placed on the interior side of the hollow plunger with the stem projecting through the aperture in the plunger seal plate towards the first chamber of the perfusion syringe 10 or 80. Preferably, the valve 94 is inserted into the plunger sealing plate 95 from the rear chamber side (cavity 91) of the plunger 90 before the two plunger pieces are press-fit together. It will be appreciated that any other suitable one-way valves or flow control devices appropriate for medical applications may be used. Accordingly, one-way flow duckbill valves, diaphragms, ball valves, or similar devices may be used. Self-sealing vent plugs preferably may be provided the hollow tubular structure of the plunger to release air and gas from the perfusion syringe in the same manner as described herein. In one embodiment as shown, the vent plugs may be disposed in the sides of plunger tube.

Figure 11:
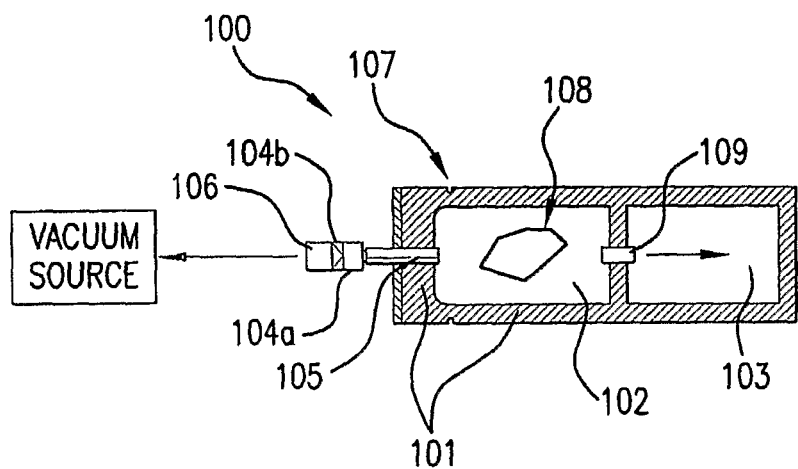
FIG. 11 is a top view of an alternative embodiment of perfusion container in the form of a flexible container having a biomaterial chamber.

An embodiment of a perfusion device with a non-rigid or flexible container is shown in FIG. 11. This perfusion device is similar in concept and function to the plunger 90 shown in FIGS. 10A&B in so far that a second chamber or cavity is provided to collect an overflow of fluid and gas/air from a first or primary chamber containing the biomaterial 108. A one-way flow control device such as without limitation a check valve 109 connects the primary and secondary chamber as in FIGS. 10A&B. This allows the first chamber to be overfilled and the excess liquid to be captured in a second chamber.

In one embodiment as shown in FIG. 11, the flexible perfusion container 100 may generally be a flexible container (e.g., a plastic bag). In one embodiment, the flexible container (e.g., a plastic bag) may be constructed with one or more plies or layers of the same or different materials. In a preferred embodiment, a perfusion container 100 has an inner liner made of low density polyethylene (LDPE) and an outer layer made of Polyethylene Terephthalate (PET).

In one embodiment, the perfusion container 100 is fabricated and sealed together via multiple seal areas 101 in a fashion to define the two chambers including a primary chamber 102 holding the biomaterial and a secondary overflow chamber 103. A Luer-type injection port 104a may be provided as described herein that connects to the primary chamber 102 holding the biomaterial via a connecting sleeve 105 as shown. This allows a medical syringe having a Luer-type fitting to be connected to the container for transferring fluid into the biomaterial chamber 102. Preferably, injection port 104a may contain a one-way flow control device such as without limitation a self-sealing spring actuated valve 104b may be provided that is operably associated with the injection port to provide a leak-proof connection. In some embodiments, the injection port may be made of polycarbonate and the connecting sleeve may be a tube formed of LDPE, polypropylene, or silicone tubing. The container is preferably sealed around both the connecting sleeve and one-way valve by seal areas 101. A Luer-type cap 106 may be provided for closing the container when not in use. A vacuum may be applied to the two-chamber perfusion container 100 in the same manner as described herein by using the medical syringe or other suitable vacuum source. In certain embodiments, it will be noted that a vent plug or similar need not be provided for the second chamber so long as the chamber capacity is sized large enough to hold the air or gas expelled from the primary chamber and any overflow of fluid. Alternatively, a vent plug may be provided for the second chamber of the container if desired. The perfusion container may have tear notches 107 to facilitate access to the biomaterial contents of the container.

Figure 12:
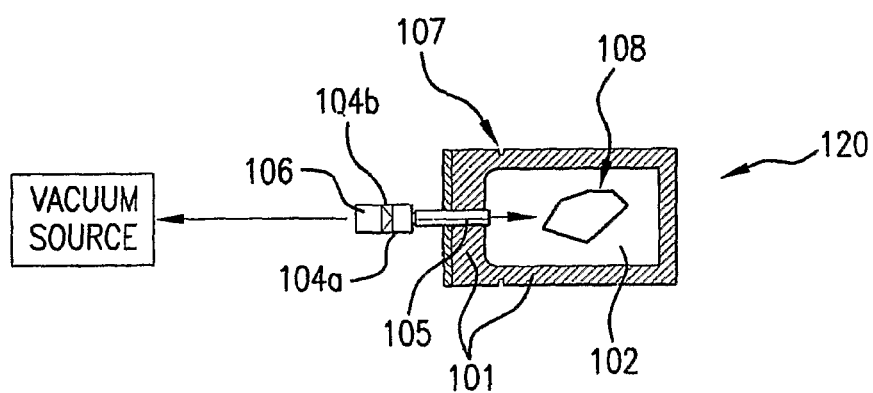
FIG. 12 is a top view of a second alternative embodiment of a perfusion container in the form of a flexible container having a biomaterial chamber.

FIG. 12 shows a flexible perfusion container 120 in the form of a container similar to the container of FIG. 11, but having only a single chamber 102 containing the biomaterial 108. However, the single-chamber container 1.02 contains vacuum packed biomaterial and would not need an additional vacuum to be applied to the biomaterial chamber. The biomaterial would be perfused by the liquid generally as soon as the liquid was introduced into the biomaterial chamber. The container, injection port, connecting sleeve, cap, and other appurtenances may be the same as described herein in connection with FIG. 11.

Figure 13A:
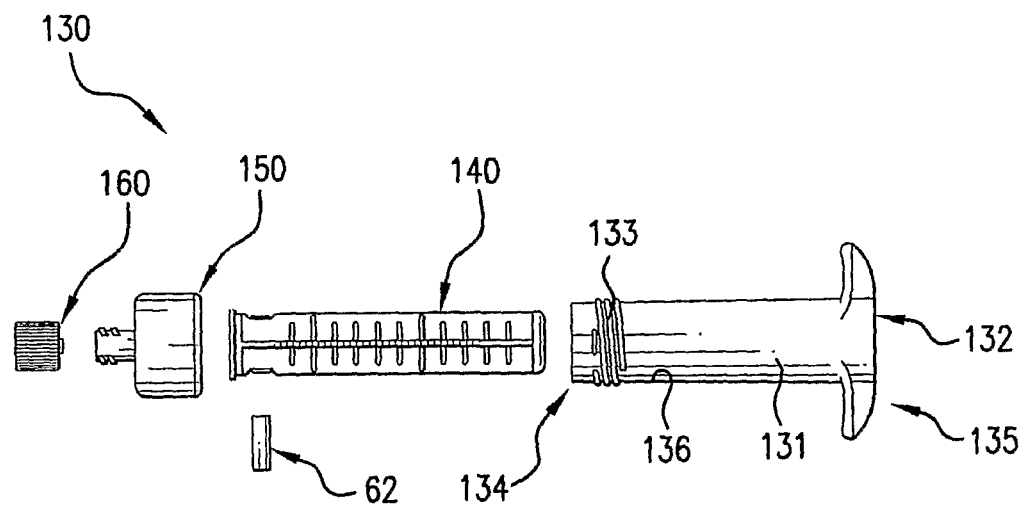
FIG. 13A shows an exploded view of the components of an alternative embodiment of a perfusion syringe having a vent in only the plunger.
Figure 13B:
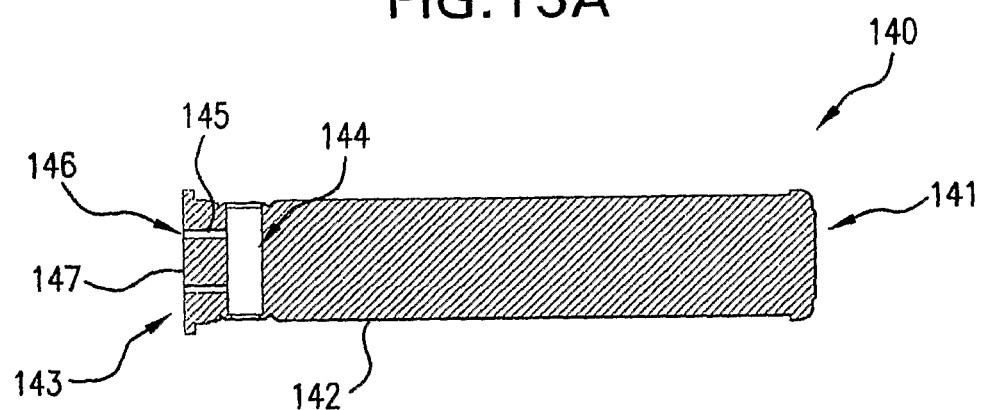
FIG. 13B is a longitudinal cross-sectional view through the plunger of the perfusion syringe of FIG. 13A.
Figure 13C:
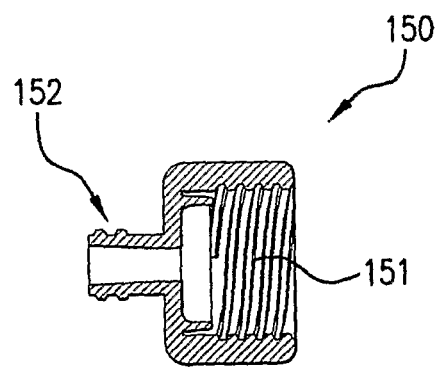
FIG. 13C is a longitudinal cross-sectional view through the end cap of the perfusion syringe of FIG. 13A.

FIGS. 13A-C shows an alternative embodiment of a perfusion syringe 130. The syringe 130 is similar in principle to syringe 10, except that vent is provided only in the plunger 140. Whereas prefusion syringe 10 has vents in both ends (i.e. vents in both the plunger 30 and end cap 20) so that either the medical or perfusion syringe 10 advantageously may be held vertically in the top or bottom position without adversely affecting the saturation of the biomaterial or expulsion of gases from the perfusion syringe, syringe 130 preferably should be vertically above the medical syringe so that liquid flow is upwards from the medical syringe through the biomaterial in syringe 130. Trapped air or gas will thus be driven upwards through syringe 130 in front of the liquid and vented through the plunger 140. In addition, whereas plunger 30 of syringe 10 has two relatively short transverse vent plug openings 41 each connected to separate internal venting passageway 43, syringe 130 has a longer single transverse vent plug opening 144 that connects to each of two internal venting passageways 145 in one embodiment as shown in FIG. 13B.

With continuing reference to FIGS. 13A-C, syringe 130 includes a tubular body 131 having a finger grip 132 on one end 135 and threads 133 on opposite end 134 for mating with complementary threads 151 on cap 150. Body 131 defines an internal chamber 136 for holding biomaterial. A plunger 140 is slidably received in body 131 and has a proximal end 141 and distal end 143. Distal end 143 includes single transverse vent plug opening 144 connected each of two internal venting passageways 145, which in turn connect to respective holes 146 in plunger sealing plate 147. The vent plug opening, venting passageways, and holes create a fluid communication pathway between syringe chamber 136 and atmosphere, similarly in principle to syringe 10. Cap 150 threadably couples to syringe body 131. Cap 150 also preferably includes a nipple 152 which preferably is configured with a Luer-type fitting to receive a complementary fitting on the medical syringe containing the fluid to be transferred to syringe 130.

It will be appreciated that in other embodiments, a single chamber perfusion container may be provided that does not contain vacuum-packed biomaterial. In this case, a vent plug or similar self-sealing device may be provided that communicates with the biomaterial chamber to allow excess air to be vented to atmosphere while the container is being filled with fluid from a medical syringe. The self-sealing device then allows a vacuum to be pulled on the biomaterial chamber for perfusing the biomaterial with the fluid in the manner described herein in connection with the perfusion syringes.

While the foregoing description and drawings represent preferred embodiments of the present invention, it will be understood that various additions, modifications and substitutions may be made therein without departing from the spirit and scope of the present invention as defined in the accompanying claims. In particular, it will be clear to those skilled in the art that the present invention may be embodied in other specific forms, structures, arrangements, proportions, sizes, and with other elements, materials, and components, without departing from the spirit or essential characteristics thereof. One skilled in the art will appreciate that the invention may be used with many modifications of structure, arrangement, proportions, sizes, materials, and components used in the practice of the invention, which are particularly adapted to specific needs and operating requirements, without departing from the principles of the present invention. Further, one skilled in the art will appreciate that one or more elements of one embodiment of the invention described herein may be combined with one or more elements of another embodiment of the invention described herein without departing from the spirit of the invention. The presently disclosed embodiments are therefore to be considered in all respects as illustrative and not restrictive, the scope of the invention being defined by the appended claims, and not limited to the foregoing description or embodiments.

What is claimed is:

1. A device for perfusing a material with a liquid comprising:
   a container including:
      an internal chamber configured to hold the material; and
      a port disposed at a distal end of the container configured to introduce a liquid from outside of the device into the internal chamber; and
   a plunger movable within the internal chamber, the plunger including:
      at least two venting passageways proximate a distal end of the plunger configured to release gas from the internal chamber;
      a transverse vent opening in fluid communication with of each of the at least two venting passageways; and
      a flow control device disposed within the transverse vent opening configured to inhibit the liquid from being released from the internal chamber when the liquid and the material are in the internal chamber.

2. The device of claim 1, wherein each of the at least two venting passageways are in fluid communication with the internal chamber.

3. The device of claim 1, wherein the flow control device includes a hydrophobic filter.

4. The device of claim 1, wherein the flow control device is configured and dimensioned to prevent the flow of liquid from the container and permit the flow of gas from the container.

5. The device of claim 1, wherein the plunger includes, proximate the distal end of the plunger, a sealing plate that is sized and configured to provide a generally leak-proof, yet slidable seal between the plunger and the container.

6. The device of claim 1, wherein the port comprises a cap threadably connected to the container, the cap further comprising a nipple configured with a fitting to receive a complementary fitting of a syringe.

7. The device of claim 1, wherein the plunger further includes, at the distal end of the plunger, an aperture that is aligned with one of the at least two venting passageways and wherein the flow control device is positioned between the aperture and a proximal end of the plunger whereby gas migrating through the aperture and into the one of the at least two venting passageways passes the flow control device before being released to the atmosphere.

8. The device of claim 1, wherein the plunger further comprises a distal plate wherein the at least two venting passageways extend axially from an outer face of the distal plate along a central axis of the plunger to the flow control device.

9. The device of claim 1, wherein the at least two vents are positioned on diametrically opposite sides of the plunger relative to a central axis of the plunger.

* * * * *

UNITED STATES PATENT AND TRADEMARK OFFICE
CERTIFICATE OF CORRECTION

PATENT NO. : 8,641,667 B2  Page 1 of 1
APPLICATION NO. : 12/089679
DATED : February 4, 2014
INVENTOR(S) : Kurek et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 133 days.

Signed and Sealed this
Twenty-second Day of September, 2015

Michelle K. Lee
*Director of the United States Patent and Trademark Office*